United States Patent [19]
Geier et al.

[11] Patent Number: 5,439,157
[45] Date of Patent: Aug. 8, 1995

[54] AUTOMATED BUTT WELD INSPECTION SYSTEM

[75] Inventors: Daniel P. Geier, Lynchburg; Kenneth R. Camplin, Forest, both of Va.

[73] Assignee: The Babcock & Wilcox Company, New Orleans, La.

[21] Appl. No.: 276,136

[22] Filed: Jul. 18, 1994

[51] Int. Cl.$^6$ .................. G01N 29/10; B23K 31/00
[52] U.S. Cl. .......................... 228/9; 228/5.7; 228/56.5
[58] Field of Search ............ 228/103, 104, 5.7, 8, 228/9, 56.5; 73/598, 600, 643

[56] References Cited

U.S. PATENT DOCUMENTS

| | | | |
|---|---|---|---|
| 3,850,028 | 11/1974 | Thompson et al. | 73/71.5 |
| 4,058,002 | 11/1977 | Moran | 73/620 |
| 4,144,766 | 3/1979 | Wehrmeister | 228/104 |
| 4,289,030 | 9/1981 | Alers et al. | 73/588 |
| 4,295,214 | 10/1981 | Thompson | 367/140 |
| 4,307,616 | 12/1981 | Vasile | 73/643 |
| 4,685,334 | 8/1987 | Latimer | 73/599 |
| 5,085,082 | 2/1992 | Cantor et al. | 228/104 |
| 5,154,081 | 10/1992 | Thompson et al. | 73/597 |

OTHER PUBLICATIONS

Technical Article by D. T. MacLauchlin, G. A. Alers and J. J. Jackson, "Detection and Measurement of Defects in Butt Welds", *Review of Progress in Quantitative Nondestructive Evaluation*, 1989, pp. 1039–1046.
Proposal #9315SA06295.017, Rev. A, dated Sep. 13, 1993, and made to Armco Steel Company, L. P. by The Taylor-Winfield Corp., Re: Automated Flash Butt Welder Inspection System for #4 Pickle Line Welder.
Proposal #CB-011-B-00, dated Sep. 24, 1993 and made to Armco Steel Company, L. P. by The Babcock & Wilcox Company; Re: Welder Diagnostic System.
Brochure entitled "Automated Butt-Weld Inspection System", published Aug. 1993, by the Taylor-Winfield Corp., Warren, Ohio.
Brochure entitled "EMAT Inspection Systems for Non-Destructive Testing", published Sep. 1993 by The Babcock & Wilcox Company, CIM Systems, Lynchburg, Va.
Brochure entitled: "Butt Weld Inspection and Weld Machine Diagnostic System", published Jul. 1994 by The Babcock & Wilcox Company, Innerspec Technologies, Lynchburg, Va.
Specification entitled "Armco Spec RES 1174 (Inquiry #M-1174-00)", dated Nov. 7, 1993, issued by Armco Steel Copany L. P. for No. 4 Pickle Line Automated Flash Butt Welder Inspection System.

*Primary Examiner*—Samuel M. Heinrich
*Attorney, Agent, or Firm*—Robert P. Bennett, Jr.; Robert J. Edwards

[57] ABSTRACT

An automated system for non-destructive inspection of a weld through the use of ultrasonic waves produced by an electromagnetic acoustic transducer (EMAT). The system includes: a computer control unit; a transport apparatus having a first EMAT for producing an ultrasonic SH shear wave and a second EMAT for receiving an ultrasonic SH shear wave reflected from a weld; a data acquisition unit and a calibration means. The computer control unit, which is in electrical communication with a welding apparatus, the transport apparatus and the data acquisition unit, coordinates the weld test with completion of the weld. An edge detection sensor, which is affixed to the transport apparatus is used to automatically position the transport apparatus for a weld scan and to signal completion of the scan. The system includes an electrostatic shield to protect the second EMAT from electromagnetic and radio frequency interference. Other new and improved electronic features permit certain system components to be remotely located from the transport apparatus and the welding apparatus.

12 Claims, 3 Drawing Sheets

AUTOMATED BUTT WELD INSPECTION SYSTEM

BACKGROUND OF THE INVENTION

1. Field of the Invention

The present invention relates in general to a weld inspection system, and more specifically to an automated system for non-destructive inspection of a weld through the use of ultrasonic waves.

2. Description of the Related Art

A variety of industries use sheet metal which is produced typically at a factory from ingots processed by a rolling mill. Ingots are heated and rolled by the mill into a long flat sheet which is then wound into a coil at the end of the mill. Thereafter, the coil is removed from the mill and shipped to other sections of the factory where further treatment processes are performed. To make these other processes have fewer interruptions, the coil is unrolled and joined at one of its ends to the end of another coil by an electric resistance weld which generally is in the form of a butt weld. Any number of coils may be welded together in such fashion, depending on the desired length of process run. Weld defects, however, can cause a weld to break during a process run, resulting in costly equipment damage, production delays and wasted material.

In order to identify and remedy weld defects before they can cause breaks and consequential production problems, non-destructive testing of the welds can be performed. An inspection device is known that uses ultrasonic waves to non-destructively test the welds shortly after they have been made. The device employs Electromagnetic Acoustic Transducers (EMAT) which are arranged to transmit and receive what are known to be SH shear waves. The SH shear waves are launched by a transmitter meander coil EMAT, and the waves travel through the sheet metal to the weld where they are reflected back through the sheet metal and are received by a separate receiver meander coil EMAT located near the transmitter. During this non-destructive test, the reflected wave produces an electrical signal in the receiver coil, which is monitored while both the transmitter coil and the receiver coil are scanned close to the surface of the sheet metal, parallel to the weld line, and over the full width of the sheet metal. During the scanning, the amplitude of the signal produced in the receiver coil is measured and used to indicate the quality of the weld.

The known device is retrofitted into a flash butt welding machine on a production line, and a motorized transport apparatus into which the transmitter and receiver coils are mounted is used to carry out each weld scan. Unlike the present invention, operation of the known device requires full-time control by a human operator, who, through the manipulation of push buttons, moves and positions the transport apparatus with the transmitter and receiver coils onto and across the sheet metal surface subsequent to the making of each weld by the welding machine. Results of the test, i.e., the measured amplitude of the receiver coil signal, are recorded on a device such as a strip chart recorder and are monitored by the human operator.

References of interest are U.S. Pat. No. 4,295,214 to Thompson, which discloses an Ultrasonic Shear Wave Transducer, and D. T. MacLauchlan, G. A. Alers and J. J. Jackson, "Detection and Measurement of Defects in Butt Welds", *Review Of Progress In Quantitative Nondestructive Evaluation*, 1989, p. 1039.

SUMMARY OF THE INVENTION

It is a general object of this invention to provide a new and improved system for non-destructive inspection of butt-type welds through the use of ultrasonic SH shear waves. The present invention has among its principal novel features the ability to automatically sense the completion of the welding process, immediately thereafter position a transport apparatus containing EMAT transmitter and receiver coils near the weld, scan the weld, receive, record, monitor and analyze the electrical signal produced in the receiver coil by the reflected SH shear wave, indicate the presence of a defect in the weld, and communicate electronically with the welding apparatus to reperform the just completed weld and/or to alter the way in which subsequent welds are made so as to avoid repetition of the observed defect.

Certain advantages over the known manually operated ultrasonic device are afforded by the present invention. The advantages include significantly improved performance, reliability and efficiency of the butt welding process and elimination of the need for an inspection device operator.

The remaining portion of this summary will point out further advantages to be derived from the present invention. A number of additional objects of the invention will also be stated.

It is an object of the present invention to automatically control the operation of the transport apparatus and to coordinate the occurrence of the welding operation and the weld inspection process. The present invention, which will be situated downstream of the welding apparatus, makes use of a computer control unit which is instrumental in providing automated control of the transport apparatus. The computer control unit has an electrical interface with the controller of the welding apparatus, as well as, with the transport apparatus and a data acquisition device. The interface to the controller of the welding apparatus is used to coordinate the sequence by which the inspection process is actuated. At the conclusion of each weld, signals are received by the computer control unit from the welding apparatus. These signals are used to coordinate the non-destructive test process with a terminal step in the welding process, known as the flash removal step, where excess weld metal is trimmed from the just completed weld. An advantage gained by coordinating the weld test and the flash removal step is minimization of the amount of time added by the testing process to the overall cycle time, i.e., the time that elapses between commencement of the welding operation and completion of the non-destructive test. In addition, the signals are employed to interlock welder and inspection processes to ensure adequate safeguards for equipment and material. Lastly, the use of the computer control unit and its integration with the welder controller eliminates the need for a human operator and thereby replaces the current art method of push button control, which requires full time operator attendance, is less time efficient and is error prone.

It is a further object of the present invention to provide a transport apparatus which has versatility of movement and which is capable of disclosing the location of any defect sensed along the weld. The transport apparatus employed by the present invention provides two-axis positioning of the EMAT transmitter and receiver coils. The transport apparatus enables inspection scanning of the sheet metal surface and safe positioning of the EMAT coils during non-inspection periods. In order to allow for variation in sheet metal thickness and to permit smooth riding of the EMAT coils on the sheet metal surface, even with surface irregularities, the transport apparatus is permitted to move in a direction generally perpendicular to the sheet metal surface at the same time that the metal surface is scanned. Real-time positional feedback is provided by the transport apparatus to a data acquisition unit which is hereinafter described. The positional feedback is used to relate weld quality data to actual position along the weld.

The present invention also utilizes a flat, plate-like, metal calibration station which provides on-line checkout and adjustment of EMAT coils and system electronics without adversely impacting production operations.

An edge detection sensor is affixed to the transport apparatus. The edge detection sensor, which is in electrical communication with the computer control unit, produces electrical signals which are used to position the EMAT coils onto the sheet metal surface at one of the sheet's edges. The sensor is also used to detect when the weld scan is complete by sensing the other of the sheet's edges. The edge detection sensor thus enables the present invention to automatically adapt to variations in the sheet metal width and position. Additionally, the edge detection sensor significantly improves collection of critical weld data at the extreme edges of a weld. Under prior art, the data collected from a weld is dependent on less reliable visual methods.

The present invention includes diagnostic capabilities with automated closed-loop control of the welding apparatus and process. Instrumentation at the welding apparatus allows monitoring of welding apparatus and process attributes that affect weld quality, including various pressures, temperatures, measurements and timed events.

It is also an object of the present invention to eliminate the need under the prior art to rely on manual and subjective review of non-destructive test results recorded on a strip chart recorder. To achieve this object, a data acquisition unit is included in the present invention. The data acquisition unit acquires, displays, stores and analyzes real-time machine and weld inspection data for the welding apparatus. The data acquisition unit is generally comprised of a computer, a computer keyboard, a video display monitor, software and electronic interconnections to the computer control unit and to the welding apparatus. Control limits for each of the monitored welding process parameters are stored on the data acquisition unit. Evaluation and disposition of each weld is performed by employing a programmable threshold for data received from non-destructive testing of each weld. During operation of the welding apparatus, an alarm indication is displayed to the welding apparatus operator if a signal which is outside of the stored control limits is received from the EMAT receiver coil. Additionally, welding apparatus or process parameters may be automatically re-adjusted through computer control. Non-destructive test data indicating a defective weld, may in turn result in an automatic re-weld operation. The data acquisition unit collects and archives empirical data that may be used for later post-analysis, historical tracking and process monitoring.

It is a further object of the present invention to safeguard the EMAT receiver coil from the effects of certain undesirable electrical interference. Unlike the prior art inspection device, the present invention includes an electrostatic shield which acts as a barrier to protect the EMAT receiver coil from Electromagnetic Interference and Radio Frequency Interference (EMI/RFI) which have been shown to pose significant problems in using EMAT instrumentation in an industrial environment where welders, grinders and other manufacturing equipment can generate deleterious electrical interference. The electrostatic shield significantly improves the performance and reliability of non-destructive testing of butt welds by reducing unwanted interference and by increasing test sensitivity.

An improved diode expander for the EMAT transmitter coil electronics is also part of the present invention. A plurality of pairs of fast switching diodes, which are part of a transmitter matching network, are placed back to back and then combined in parallel and in series to form a diode network which couples the transmitter pulses with very little loss and which blocks any low level spurious noise from the transmitter circuitry when the transmitter is off. This allows the EMAT receiver coil to receive incoming signals without interference from noise generated by the transmitter coil circuitry.

The present invention also employs a novel, remote preamplifier and an impedance matching circuit which enable the EMAT coils to be operated at distances greater than 100 feet from other electronic instrumentation which is part of the invention. The remote preamplifier and impedance matching circuit decrease RF power losses in cables and minimize the impedance mismatch between the RF power amplifier and the EMAT coil for a variety of cable lengths. The preamplifier increases most signal responses to levels that are much greater than EMI signals that might enter the system through the receiver cables. Any EMI attributed to long cable length is negligible when compared to signals received from the EMAT receiver coil. The preamplifier has circuitry which has been designed in a package that is small enough to be attached to the EMAT with relatively little increase in total EMAT size and weight. The present invention thus enhances the utility and versatility of the known pulsed magnet inspection system. Unlike the prior art, electronic instrumentation of the present invention can be located in an isolated station hundreds of feet removed from the hostile environment of the factory where the EMAT coils must be located.

Also part of the present invention, is a new magnet pulser/switching circuit which generates high current pulses necessary to charge pulsed magnets.

The various features of novelty which characterize the present invention are pointed out with particularity in the claims annexed to and forming a part of this disclosure. For a better understanding of the present invention, its operation advantages and specific objects attained by its uses, reference is made to the accompanying drawings and descriptive matter in which the preferred embodiment of the invention is illustrated.

DESCRIPTION OF PREFERRED EMBODIMENT

The present invention permits automated inspection of butt welds typically employed to join the ends of two sheet metal coils. A typical sheet metal production and treatment line on which the present invention may be utilized is comprised of a rolling mill, a plurality of roughing stands, a plurality of finishing stands, a first shearing apparatus, a welding apparatus, a temper mill, a pickling apparatus, a water rinse apparatus, a drying apparatus, a second shearing apparatus, a side splitter apparatus and a tandem cold mill. Frequently, a long flat sheet of metal produced by the rolling mill will be wound into a coil after passing through the finishing stands. The coil will then be transported to the first shearing apparatus located at another section of the factory and the end of that coil will be joined at the welding apparatus to the trailing end of another earlier transported coil which, for the most part, has already passed through a number of processing and treatment stations downstream of the welding apparatus. The location where the non-destructive weld test is made lies between the welding apparatus and the temper mill.

Figure 1:
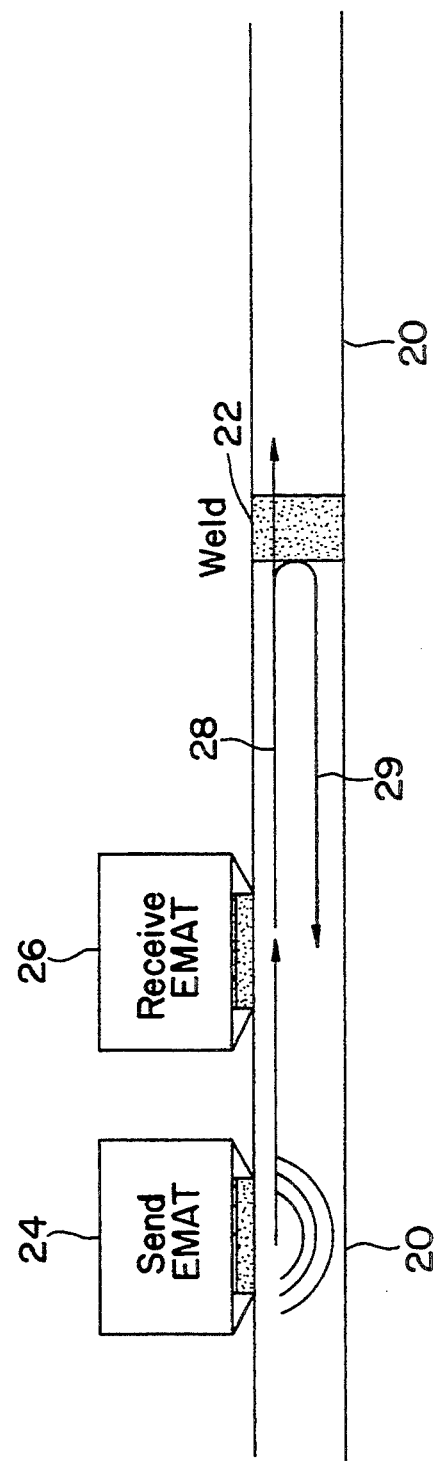
FIG. 1 is a schematic illustration displaying, in cross section, end portions of two sheet metal coils, joined by a butt weld and EMAT transmitter and receiver coils positioned near the weld, along with a one-dimensional path of travel of transmitted and reflected ultrasonic waves within the sheet metal.

FIG. 1 provides a cross sectional visualization of end portions (20) of two sheet metal coils, which are connected by a butt weld (22) made by the welding apparatus. Also shown in FIG. 1, are an EMAT transmitter coil (24) and an EMAT receiver coil (26), both of which are positioned just downstream of the butt weld (22) on a surface of the end portion (20) of one of the sheet metal coils. EMAT transmitter coil (24) produces an ultrasonic SH shear wave (28) which travels through end portion (20) toward butt weld (22) where a fraction of the SH shear wave (28) passes through the butt weld (22) and a fraction of the wave passes back through the end portion (20) and toward the EMAT receiver coil (26) as a reflected wave (29).

Figure 2:
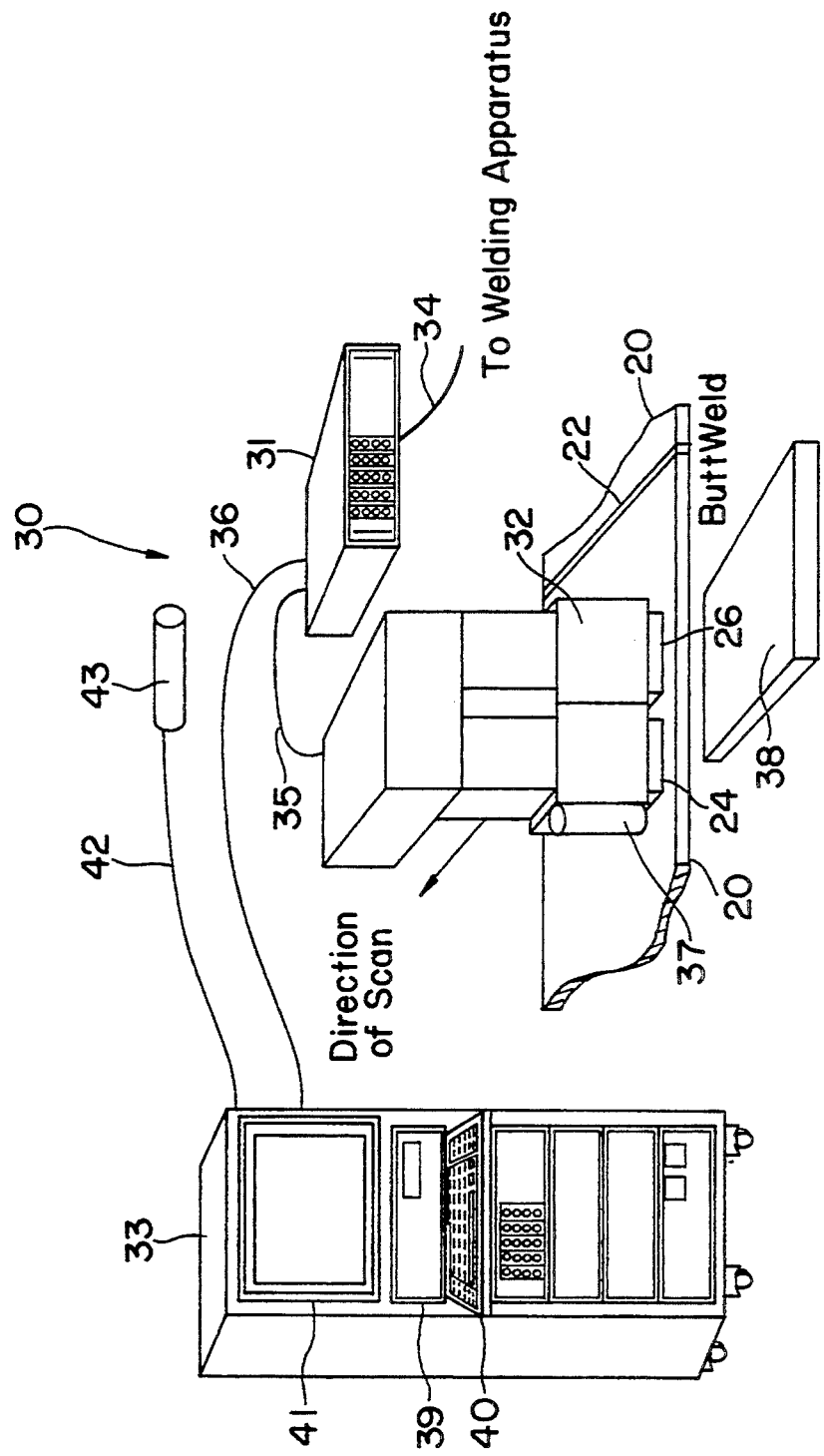
FIG. 2 is an illustration of the present invention, pointing out the principal components thereof.

FIG. 2 illustrates the fundamental components of the present invention. The present invention has a computer control unit (31) which is in electrical communication with the welding apparatus, an L-shaped transport apparatus (32) and a data acquisition unit (33). A first cable (34) provides the electrical connection between the computer control unit (31) and the welding apparatus. A second cable (35) electrically connects the computer control unit (31) to the transport apparatus (32), and a third cable (36) links the computer control unit (31) to the data acquisition unit (33). The transport apparatus (32), which is positioned just down stream of the butt weld (22), has housed within one of its ends the EMAT transmitter coil (24) and the EMAT receiver coil (26). An edge detection sensor (37) is affixed to the transport apparatus in proximity of the EMAT transmitter coil (24). The edge detection sensor (37), which is in electrical communication with the computer control unit (31), is used to position the EMAT coils (24) and (26) at an edge of the end portion (20) of one of the sheet metal coils and to detect when the weld scan is complete.

Also shown in FIG. 2, is a flat, plate-like metal calibration station (38) which is used with the transport apparatus (32) to provide on-line checkout and adjustment of the EMAT transmitter coil (24) and the EMAT receiver coil (26) as well as other system electronics. The data acquisition unit (33) includes a computer (39), a computer keyboard (40), a video display monitor (41) and a cable (42) having a connector (43), both of which provide for electrical connection of the data acquisition unit (33) to the welding apparatus.

Figure 3:
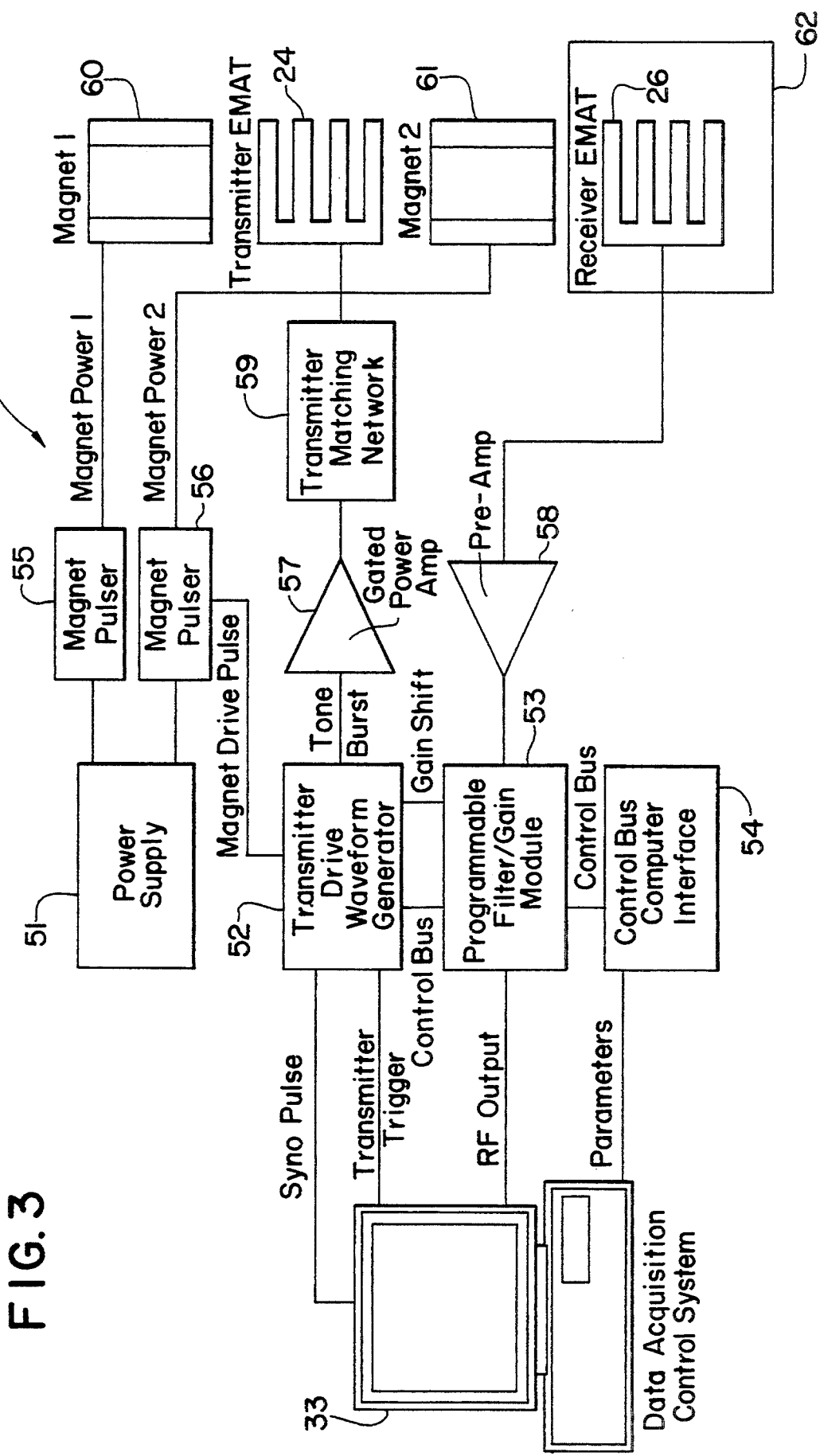
FIG. 3 is a schematic drawing of the electronics employed with the EMAT transmitter and receiver coil of the present invention.

FIG. 3 provides a schematic illustration of the electronics employed with the EMAT transmitter coil (24) and the EMAT receiver coil (26). The electronics (50) include a power supply (51), a transmitter drive waveform generator (52), a programmable filter/gain module (53), a control bus computer interface (54), a first magnet pulser (55), a second magnet pulser (56), a gated power amp (57), a pre-amp (58), a transmitter matching network (59), a first magnet (60), a second magnet (61) and an electrostatic shield (62). The power supply (51) provides electric current to the first magnet pulser (55) and to the second magnet pulser (56). The first magnet pulser (55) is connected to first magnet (60), and the second magnet pulser (56) is linked to second magnet (61). First magnet pulser (55) and second magnet pulser (56) generate high current pulses which are employed to charge first magnet (60) and second magnet (61), respectively.

The transmitter drive waveform generator (52) is linked electrically to the data acquisition unit (33), the second magnet pulser (56), the gated power amp (57) and the programmable filter/gain module (53). To the transmitter wave form generator (52) from the data acquisition unit (33), a sync pulse and a transmitter trigger are provided. From the transmitter wave form generator (52), a magnet drive pulse is provided to the second magnet pulser (56), a tone burst is provided to the gated power amp (57) and a gain shift is supplied to the programmable filter/gain module (53).

In addition to being linked to the transmitter drive waveform generator (52), the programmable filter/gain module (53) is in electrical,communication with the data acquisition unit (33), the pre-amp (58) and the control bus computer interface (54). To the programmable filter/gain module (53), a control bus is provided from the control bus computer interface (54). A RF output is supplied from the programmable filter/gain module (53) to the data acquisition unit (33).

The control bus computer interface (54), in addition to having an electrical connection with the programmable filter/gain module (53), has an electrical link to the data acquisition unit (33). Welding process parameters which have been stored on the data acquisition unit (33) are provided to the control bus computer interface (54).

The gated power amp (57) is joined to the transmitter matching network (59) which is in turn linked to the EMAT transmitter coil (24).

The pre-amp (58) is in electrical communication with the EMAT receiver coil (26) which is located within an electrostatic shield (62) and which receives the reflected SH shear wave (29) from the butt weld (22). The pre-amp (58) and the transmitter matching network (59) enable the EMAT coils (24 and 26) to be operated at distances greater than 100 feet from other electronic instrumentation of the present invention.

While a specific embodiment of the invention has been shown and described in detail to illustrate the application of the principles of the invention, it will be understood that the invention may be embodied otherwise without departing from such principles.

What is claimed is:

1. An automated weld inspection system for nondestructively examining a butt weld used to join two coils of sheet metal end-to-end, the inspection system comprising:
   a computer control unit for coordinating the making of a weld by a welding apparatus and the examining of the weld by the weld inspection system;
   a transport apparatus having a first and a second electromagnetic acoustic transducer (EMAT) attached to and housed within the transport apparatus;
   an edge detection sensor affixed to the transport apparatus in proximity of either the first or the second EMAT;
   a data acquisition unit for receiving, storing, displaying and analyzing information provided from the computer control unit and for transmitting information to the welding apparatus; and
   a calibration means for making checks of and adjustments to the weld inspection system.

2. A system according to claim 1, wherein the computer control unit is in electrical communication with the welding apparatus, the transport apparatus and the data acquisition unit.

3. A system according to claim 2, wherein the data acquisition unit is in electrical communication with the welding apparatus.

4. A system according to claim 3, wherein the first EMAT produces an ultrasonic SH shear wave which is transmitted through an end portion of a first sheet metal coil toward a butt weld joining the end portion of the first sheet metal coil to an end portion of a second sheet metal coil.

5. A system according to claim 4, wherein the second EMAT receives an ultrasonic SH shear wave which is reflected from the butt weld and which produces an electrical signal in the second EMAT, which signal is monitored for an indication of a weld defect.

6. A system according to claim 5, wherein the edge detection sensor is in electrical communication with the computer control unit for positioning the first EMAT and the second EMAT in proximity of the butt weld and at an edge of the first sheet metal coil and for detecting an opposite edge of the first sheet metal coil upon completion of a scan of the butt weld, made by moving the first EMAT and the second EMAT across the surface of the first sheet metal coil and parallel to the butt weld.

7. A system according to claim 6, wherein the data acquisition unit further comprises:
   a computer, such as a 486-based IBM/AT, having software suitable for acquiring, storing, displaying, monitoring and analyzing real-time data provided from the welding apparatus and from the computer control unit;
   a computer keyboard; and
   a video display monitor.

8. A system according to claim 7, wherein the second EMAT has an electrostatic shield, for protecting the second EMAT from electromagnetic interference and radio frequency interference.

9. A system according to claim 8, wherein the first EMAT has a diode expander comprised of a plurality of pairs of fast switching diodes placed back-to-back and then combined in parallel and in series to form a diode network.

10. A system according to claim 9, wherein the first EMAT is in electrical communication with an impedance matching circuit and the second EMAT is in electrical communication with a preamplifier.

11. A system according to claim 10, wherein the first EMAT and the second EMAT include an electromagnet which is in electrical communication with a magnet pulser which produces high current pulses of electrical energy that is used to charge the electromagnets.

12. A system according to claim 11, wherein the calibration means is a flat, plate-like piece of metal having known properties and characteristics.

* * * * *